(12) United States Patent
Chen et al.

(10) Patent No.: US 11,534,240 B2
(45) Date of Patent: Dec. 27, 2022

(54) INTELLIGENT MONITORING SYSTEM FOR PELVIC FRACTURE REDUCTION

(71) Applicant: CHINESE PLA GENERAL HOSPITAL, Beijing (CN)

(72) Inventors: Hua Chen, Beijing (CN); Peifu Tang, Beijing (CN)

(73) Assignee: CHINESE PLA GENERAL HOSPITAL, Beijing (CN)

( * ) Notice: Subject to any disclaimer, the term of this patent is extended or adjusted under 35 U.S.C. 154(b) by 0 days.

(21) Appl. No.: 17/431,266

(22) PCT Filed: Feb. 13, 2020

(86) PCT No.: PCT/CN2020/075110
§ 371 (c)(1),
(2) Date: Aug. 16, 2021

(87) PCT Pub. No.: WO2020/164548
PCT Pub. Date: Aug. 20, 2020

(65) Prior Publication Data
US 2022/0039870 A1 Feb. 10, 2022

(30) Foreign Application Priority Data
Feb. 15, 2019 (CN) .......................... 201910116464.1

(51) Int. Cl.
*A61B 34/10* (2016.01)
*A61B 34/20* (2016.01)
(Continued)

(52) U.S. Cl.
CPC .............. *A61B 34/10* (2016.02); *A61B 34/20* (2016.02); *A61B 90/36* (2016.02);
(Continued)

(58) Field of Classification Search
CPC ......... A61B 34/10; A61B 34/20; A61B 90/36; A61B 2034/105; A61B 2034/2055; A61B 2034/256; A61B 2090/365
See application file for complete search history.

(56) References Cited

U.S. PATENT DOCUMENTS

2006/0094951 A1* 5/2006 Dean ....................... G06T 17/10
600/407
2012/0010617 A1* 1/2012 Ramos Maza ..... A61B 17/8897
606/70
(Continued)

FOREIGN PATENT DOCUMENTS

CN 105105841 A 12/2015
CN 105434029 A 3/2016
(Continued)

OTHER PUBLICATIONS

International Search Report (and its English translation, 6 pages) and Written Opinion (4 pages) from PCT Application No. PCT/CN2020/075110 dated May 14, 2020).

*Primary Examiner* — Patricia J Park
(74) *Attorney, Agent, or Firm* — Harness, Dickey & Pierce, P.L.C.; Anthony G. Fussner (57) ABSTRACT

An intelligent monitoring system for pelvic fracture reduction, comprising a sample fracture model database, a patient pelvic fracture data acquisition unit, a reduction situation monitoring unit and a mixed reality data fusion processing unit, the sample fracture model database stores a plurality of sample fracture models, the patient pelvic fracture data acquisition unit uses magnetic navigation and positioning technology to collect patient pelvic location information data in real-time and upload it to the mixed reality data fusion processing unit, the mixed reality data fusion processing unit automatically invokes the sample fracture model in the sample fracture model database corresponding to patient pelvic fracture condition and matches the patient pelvic location information data with the sample fracture model using mixed reality technology to form an intelligent fracture model for the patient's pelvic fracture state, the reduction situation monitoring unit loads and displays images of the intelligent fracture model in different positions in real-time and monitors the reduction situation of different positions of the patient's pelvis in real-time. The system enhances treatment effect and reduces personnel radiation.

13 Claims, 4 Drawing Sheets

(51) Int. Cl.
   *A61B 90/00*   (2016.01)
   *A61B 34/00*   (2016.01)
(52) U.S. Cl.
   CPC ... *A61B 2034/102* (2016.02); *A61B 2034/105* (2016.02); *A61B 2034/2055* (2016.02); *A61B 2034/256* (2016.02); *A61B 2090/365* (2016.02)

(56) References Cited

U.S. PATENT DOCUMENTS

| | | | | |
|---|---|---|---|---|
| 2013/0033700 | A1* | 2/2013 | Hallil | A61N 5/1071 378/63 |
| 2014/0222409 | A1* | 8/2014 | Efrat | G01R 33/10 703/13 |
| 2014/0328460 | A1  | 11/2014 | Egli et al. | |
| 2016/0191887 | A1* | 6/2016 | Casas | H04N 13/279 348/47 |
| 2019/0122330 | A1* | 4/2019 | Saget | A61F 2/4607 |
| 2021/0015560 | A1* | 1/2021 | Boddington | G16H 30/40 |

FOREIGN PATENT DOCUMENTS

| | | | |
|---|---|---|---|
| CN | 109820590 A | | 5/2019 |
| WO | WO2018/167369 | * | 9/2018 |
| WO | WO-2018167369 A1 | | 9/2018 |

\* cited by examiner

INTELLIGENT MONITORING SYSTEM FOR PELVIC FRACTURE REDUCTION

This patent application is a U.S. national stage filing under 35 U.S.C. § 371 of International Application No. PCT/CN2020/075110 filed Feb. 13, 2020 (published as WO 2020/164548 on Aug. 20, 2020), which claims the benefit of and priority to Chinese application number 201910116464.1 filed Feb. 15, 2019. The disclosures of the applications identified in this paragraph are incorporated herein by reference in their entirety.

TECHNICAL FIELD

The present invention relates to the medical technical field of pelvic reduction, in particular to an intelligent monitoring system for pelvic fracture reduction.

BACKGROUND TECHNIQUE

Pelvic fracture (or acetabular fracture) is a serious civilian injury and battlefield trauma with a high disability, a high mortality and a high incidence, more than half of pelvic fractures are accompanied by complications and multiple injuries, seriously threatening lives of sick and wounded, and the death rate of pelvic fractures without merging soft tissue or internal organ injury is about 10.8%, and the death rate of complex pelvic fractures can even reach 30%-50%. And existing treatment technology of conventional incision surgical treatment method has many problems, especially in the standard treatment usually repaired by incision reduction surgery and fixation, there exists problems with large wounds, much bleeding, and great difficulty of reset and fixation reduction and fixation, many patients/noneffectives's bleeding reached tens of thousands of milliliters during surgery, even some patients/noneffectives can't tolerate surgery and leave us; Of course, there are also some patients/noneffectives easy to miss the opportunity of surgical treatment because of these problems, and eventually left with permanent disability.

In order to solve above situation, the domestic existing minimally invasive fast repair technology of pelvic fracture has begun to be used in clinical practice, but the minimally invasive fast repair technology of pelvic fracture in the process of clinical use met many bottleneck problems such as: How to achieve closed fracture reduction without cutting or small mouth, and then complete the stable fixation of fracture through minimally invasive method? How to reduce operation difficulty and shorten operation time? How to keep precise operation fixed time in advance, and also to ensure the life safety of patients? How to minimize radiation exposure damage to medical staff and patients or directly reduce radiation exposure?

Even 301 hospital medical team for above problem has been studied and designed the pelvis minimally invasive closed reduction system, under the two-dimensional perspective image surveillance for pelvic closed reduction treatment, to some extent, it has realized the minimally invasive surgery for pelvic fracture reduction treatment, but the technology in clinical application still need to patients and medical staff must always be in a perspective environment (ray in the irradiation environment), that is, patients and medical staff will be exposed to radiation (such as fluoroscopy X ray exposure, etc.) and then be damaged by radiation exposure. Therefore, how to reduce radiation exposure is a major problem to be solved urgently at present.

SUMMARY OF THE INVENTION

The invention in view of the existing technology in the pelvis fracture reduction treatment in the clinical application of patients and medical staff will be radiation damage defects, provides an intelligent monitoring system for pelvic fracture reduction, the system introduces a sample pelvis to simulate data from human body pelvic fracture and establishes a sample fracture model, then, magnetic navigation and positioning technology was used to collect real-time patient pelvic location information, using mixed reality technology to form an intelligent fracture model for state of the patient's pelvic fracture and to monitor the reduction of the patient's pelvis in different positions in real time, it can realize closed and accurate reduction of seriously displaced pelvic fracture and reduce radiation injury to the patient and medical staff.

The technical solution of the present invention is as follows:

An intelligent monitoring system for pelvic fracture reduction, comprising a sample fracture model database, a patient pelvic fracture data acquisition unit, a mixed reality data fusion processing unit and a reduction situation monitoring unit, the sample fracture model database, the patient pelvic fracture data acquisition unit and the reduction situation monitoring unit are connected with the mixed reality data fusion processing unit, the sample fracture model database stores a plurality of sample fracture models that is established by data of human body pelvic fracture simulated by a sample pelvis based on automatic segmentation algorithm, the patient pelvic fracture data acquisition unit uses magnetic navigation and positioning technology to collect patient pelvic location information data in real-time and upload it to the mixed reality data fusion processing unit, the mixed reality data fusion processing unit automatically invokes the sample fracture model in the sample fracture model database corresponding to patient pelvic fracture condition according to the patient pelvic location information data and matches the patient pelvic location information data with the sample fracture model using mixed reality technology to form an intelligent fracture model for the patient's pelvic fracture state, the reduction situation monitoring unit loads and displays images of the intelligent fracture model in different positions in real-time and monitors the reduction situation of different positions of the patient's pelvis in real-time through multiple monitoring images.

Preferably, the intelligent monitoring system for pelvis fracture reduction, further comprising a pelvic fracture simulation data acquisition unit, a data processing analysis unit and a model establishment unit in turn, the model establishment unit is connected to the sample fracture model database, the pelvic fracture simulation data acquisition unit collects data from the sample pelvis to simulate human body pelvic fracture, and the data processing analysis unit is based on the artificial intelligence technology for automatic analysis and processing, the model establishment unit uses analyzed fracture simulation data and based on automatic segmentation algorithm to establish a number of sample fracture models, all the sample fracture models are stored in the sample fracture model database.

Preferably, the pelvic fracture simulation data acquisition unit collects fracture simulation data from several angles by comprising, but not limited to, photographs, two-dimensional perspective, or scanning way, the sample pelvis comprises, but not limited to, an artificial pelvis, an animal pelvis, or a cadaver pelvis.

Preferably, the patient pelvic fracture data acquisition unit collects the pelvic location information data in real-time through the magnetic navigation and positioning technology by magnetic detectors close to the pelvic surface of the patient and the optical tracking technology by an optical locator connected to the magnetic detectors to realize the patient pelvic positioning, the positioning location accuracy is not less than 5 mm and the positioning angle accuracy is not less than 5°, the pelvic location information data of the patient comprises but is not limited to the location information data of each bone block, implant and peripheral operating rod, reduction frame and operating bed in the patient's pelvis.

Preferably, the mixed reality data fusion processing unit matches the coordinate system and the relative position relationship between the implant, operating rod, reduction frame and operating bed when matching the patient pelvic location information data with the sample fracture model using mixed reality technology, and matching process is carried out by automated non-rigid image registration technology.

Preferably, the patient pelvic fracture data acquisition unit receives the pelvic location information of the patient after the reduction operation of the patient's pelvic fracture by medical personnel or intelligent robot, the mixed reality data fusion processing unit also uses automated diagnostic techniques to diagnose overfitting after received patient pelvic fracture reduction operation.

Preferably, the mixed reality data fusion processing unit loads the constructed intelligent fracture model for the patient pelvic fracture state for muscle attachment condition, based on the human body tissue bounding box tree method realize automatic avoidance of the important human anatomy during the operating rod implantation process.

Preferably, when the patient pelvic fracture data acquisition unit receives the patient pelvic location information after the reduction operation of the patient pelvic fracture by the intelligent robot, the mixed reality data fusion processing unit also performs intelligent reduction clinical path planning in real-time according to results of deep learning of the sample fracture model and the intelligent fracture model.

Preferably, the patient pelvic fracture data acquisition unit receives the patient pelvic location information after the reduction operation of the patient pelvic fracture by intelligent mechanical arms loaded with muscle force.

Preferably, the reduction situation monitoring unit monitors the position of the patient's pelvis in real-time, including any three or more positions combinations of pelvic front position, pelvic entrance position, pelvic exit position, obturator oblique position, iliac oblique position, LC-2 full-length image, teardrop image, obturator exit position, iliac entrance position, the sacroiliac joint image entrance position, the sacroiliac joint image exit position, the iliac wing image, the lateral pelvic image ICD line position, and the posterior column position of the pelvis lateral image.

The technical effects of the present invention are as follows:

The invention relates to a kind of intelligent monitoring system for pelvis fracture reduction, set the sample fracture model database, the patients pelvic fracture data acquisition unit, the mixed reality data fusion processing unit and the reduction situation monitoring unit, the sample fracture model database introduces a sample pelvis to simulate data from human body pelvic fracture and establishes a sample fracture model based on automatic segmentation algorithm, then, magnetic navigation and positioning technology was used by the patients pelvic fracture data acquisition unit to collect real-time patient pelvic location information, the mixed reality data fusion processing unit uses mixed reality technology to form an intelligent fracture model for state of the patient's pelvic fracture and the reduction situation monitoring unit monitors the reduction of the patient's pelvis in different positions in real time, that is to say, all kinds of fractures were prepared on the pelvic model to be placed in all kinds of possible fracture displacement situations, the reduction guidance of displaced bone block was realized by computer simulation to improve the reduction accuracy. With the combination of automatic segmentation algorithm, magnetic navigation and positioning technology, artificial intelligence technology and mixed reality technology, all components work together to realize the intelligent monitoring of pelvic fracture reduction, even seriously displaced pelvic fracture can be reduced precisely, and the closed reduction of pelvic fracture can meet the requirements of minimally invasive orthopedic surgery, at the same time, it can meet the comprehensive requirements of minimally invasive orthopedic surgery on its operation space, occupied space, flexibility, load, stability and other performance. And most importantly, there is no need to take X-ray images during the operation, which completely solves the problem that both patients and medical staff will be injured by radiation exposure in the clinical application of fracture pelvic reduction treatment, so as to reduce the radiation injury to patients and medical staff and protect the safety of both doctors and patients.

Preferably, the system comprises the sample fracture model database, the patient pelvic fracture data acquisition unit, the mixed reality data fusion processing unit and the reduction situation monitoring unit, as well as a pelvic fracture simulation data acquisition unit, a data processing analysis unit and a model establishment unit successively, the pelvic fracture simulation data acquisition unit collects data from the sample pelvis to simulate human body pelvic fracture, and the data processing analysis unit is based on the artificial intelligence technology for automatic analysis and processing, the model establishment unit uses analyzed fracture simulation data and based on automatic segmentation algorithm to establish a number of sample fracture models, and then all the sample fracture models are stored in the sample fracture model database, and further optimally, the pelvic fracture simulation data acquisition unit collects fracture simulation data from several angles by comprising, but not limited to, photography, two-dimensional perspective, or scanning way, at the same time optimization, the sample pelvis comprises artificial pelvis, animal bodies pelvis or the cadaver pelvis as so on, big data analysis and artificial intelligence technology are innovatively utilized, modeling is more accurate and reliable.

Preferably, the patient pelvic fracture data acquisition unit collects the pelvic location information data in real-time through the magnetic navigation and positioning technology by magnetic detectors close to the pelvic surface of the patient and the optical tracking technology by an optical locator connected to the magnetic detectors, the pelvic location information data comprises but is not limited to the location information data of each bone block, implant and peripheral operating rod, reduction frame and operating bed in the patient's pelvis, that is only using the magnetic navigation and positioning technology and the optical tracking technology to obtain pelvic fracture conditions, which allows medical staff to require small wounds into several implants or operating rods without patient surgery, it can accurately determine the fracture of the patient, and avoid the problems of large incision and large loss of blood in the previous pelvic reduction surgery.

Preferably, the mixed reality data fusion processing unit also performs intelligent reduction clinical path planning in real-time according to results of deep learning of the sample fracture model and the intelligent fracture model, so as to automatically find the optimization of clinical surgery path (note that surgery path must be to unlock of pelvic bone block first, push and pull of the reentry shift operation after unlocking), the operation path is shortest to avoid secondary injury caused by large range of movement, and at the same time, important human body anatomical structures or tissues such as blood vessels, nerves and bone blocks are effectively avoided to avoid unnecessary injuries, save operation time and improve surgical treatment effect.

Preferably, the patient pelvic fracture data acquisition unit receives the patient pelvic location information after the reduction operation of the patient pelvic fracture by intelligent mechanical arms loaded with muscle force, that is to say, the intelligent robot adopts the intelligent mechanical arm based on the muscle force loading method to simulate the operation strength of the medical staff, after simulating the operation strength of the medical personnel with the intelligent mechanical arm, the surgical operation according to the intelligent reduction path realizes the whole intelligent automatic operation of the whole operation process, the medical personnel can not enter the operating room or only occasionally observe the medical images displayed in the reduction situation monitoring unit in the operating room, to avoid the ray irradiation of the medical personnel and ensure the safety of the medical personnel.

Preferably, the reduction situation monitoring unit monitors the position of the patient's pelvis in real-time including a combination of more than three in the common 14 positions, through the real-time observations, can effectively judge the restoration of patient pelvic fractures, if the observation of only one or two positions are successful and the reset of the third position has not been realized, the actual reduction of stereoscopic pelvis is unsuccessful, if the observations of three or more positions are successful, the actual reduction of the stereoscopic pelvis is successful, this fully solves problem of three-dimensional operation space control caused by the lack of information of real-time two-dimensional medical images, and realizes the accurate guidance of stereoscopic reduction.

Reference Numbers in the Drawings are Listed as Follows:
1—optical locator ball; 2—magnetic detector.

DETAILED DESCRIPTION OF THE PREFERRED EMBODIMENTS

The present invention is further described with reference to the accompanying drawings.

Figure 1:
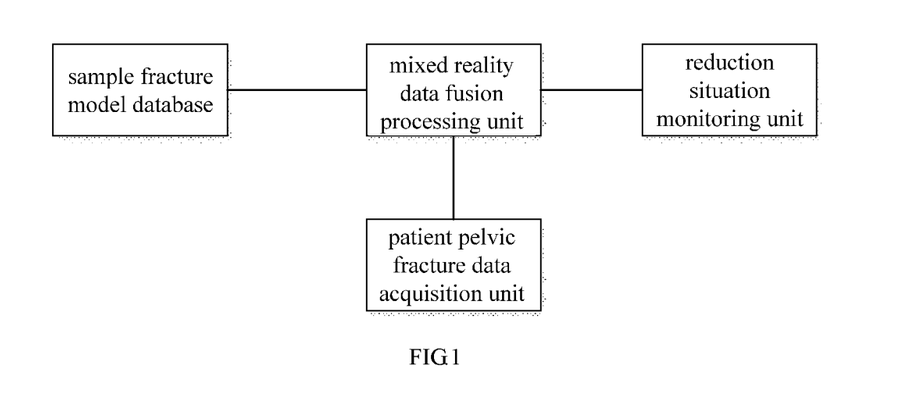
FIG. 1 is a structural schematic diagram of an intelligent monitoring system for pelvic fracture reduction of the invention.

The invention relates to an intelligent monitoring system for the reduction of pelvic fracture, which comprises a sample fracture model database, a patient pelvic fracture data acquisition unit, a mixed reality data fusion processing unit and a reduction situation monitoring unit, as shown in FIG. 1, the sample fracture model database, the patient pelvic fracture data acquisition unit and the reduction situation monitoring unit are connected with the mixed reality data fusion processing unit, the sample fracture model database stores a plurality of sample fracture models that is established by data of human body pelvic fracture simulated by a sample pelvis based on automatic segmentation algorithm, that can pass in the sample pelvis (which can be understood as false pelvis, specimen pelvis) preparation or simulation on each type of fractures in a variety of possible fracture shift condition, thus fully introduced all kinds of pelvic fractures, to be sure, the sample pelvic fracture model database can be instant data collection and modeling database, it can also be original historical database of the called hospital, and the database can exist alone as a product; the patient pelvic fracture data acquisition unit uses magnetic navigation and positioning technology to collect patient pelvic location information data in real-time and upload it to the mixed reality data fusion processing unit, the mixed reality data fusion processing unit automatically invokes the sample fracture model in the sample fracture model database corresponding to patient pelvic fracture condition according to the patient pelvic location information data and matches the patient pelvic location information data with the sample fracture model using mixed reality technology to form an intelligent fracture model for the patient's pelvic fracture state, reduction navigation of the displacement bone block is realized by computer simulation and then improves reduction accuracy, the reduction situation monitoring unit loads images displaying the intelligent fracture model in different positions in real-time and monitors the reduction situation of different positions of the patient's pelvis in real-time through multiple monitoring images, so that the medical staff can observe dynamic change in real-time, provide reliable basis for the diagnosis of operation. The components of the invention work together and combine the automatic segmentation algorithm, magnetic navigation and positioning technology, artificial intelligence technology and mixed reality technology etc to realize the intelligent monitoring of the reduction of pelvic fracture. Even seriously displaced pelvic fracture can be reduced accurately, and the closed reduction of pelvic fracture can meet the requirements of minimally invasive orthopedic surgery. At the same time, it can meet the comprehensive requirements of minimally invasive orthopedic surgery on its operation space, occupied space, flexibility, load, stability and other performance. And most importantly, there is no need to take X-ray images during the operation, which completely solves problems that both patients and medical staff will be injured by radiation exposure in the clinical application of fracture pelvic reduction treatment, so as to reduce the radiation injury to patients and medical staff and protect the safety of both doctors and patients.

Figure 2:
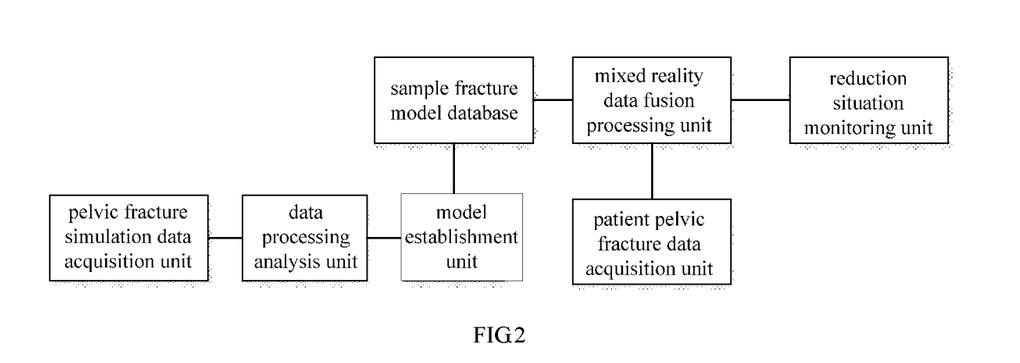
FIG. 2 is the schematic diagram of the preferred structure of an intelligent monitoring system for pelvic fracture reduction of the invention.

The optimal structure diagram of the pelvic fracture reduction intelligent monitoring system of the invention is shown in FIG. 2. The system comprises the sample fracture model database, the patient pelvic fracture data acquisition unit, the mixed reality data fusion processing unit and the reduction situation monitoring unit, as well as a pelvic fracture simulation data acquisition unit, a data processing analysis unit and a model establishment unit successively, the model establishment unit is connected to the sample fracture model database, the pelvic fracture simulation data acquisition unit collects data from the sample pelvis to simulate human body pelvic fracture, and the data processing analysis unit is based on the artificial intelligence technology for automatic analysis and processing, the model establishment unit uses analyzed fracture simulation data and based on automatic segmentation algorithm to establish a number of sample fracture models, and then all the sample fracture models are stored in the sample fracture model database, and further optimally, the pelvic fracture simulation data acquisition unit collects fracture simulation data from several angles by comprising, but not limited to, photography, two-dimensional perspective, or scanning way, at the same time optimization, the sample pelvis comprises artificial pelvis, animal bodies pelvis or the cadaver pelvis as so on, such as this example optimization uses of artificial pelvis photograph from several angles, two-dimensional perspective or scanning, in turn, create a two-dimensional CT image of the multiple perspectives, or virtual projection for the two-dimensional CT images to generate digital images, then the data processing analysis unit based on artificial intelligence techniques for automated analysis processing, then, based on automatic segmentation algorithm and fast finite element model mesh generation method, several individual sample fracture models were established by the model establishment unit, and then stored in the sample fracture model database, big data analysis and artificial intelligence technology were used to make the modeling more accurate and reliable.

Preferably, the patient pelvic fracture data acquisition unit collects the pelvic location information data in real-time through the magnetic navigation and positioning technology by magnetic detectors close to the pelvic surface of the patient and the optical tracking technology by an optical locator connected to the magnetic detectors to realize the patient pelvic positioning, the optical tracking technology further comprises 3D motion capture technology, the positioning location accuracy is not less than 5 mm and the positioning angle accuracy is not less than 5°, the pelvic location information data of the patient comprises but is not limited to the location information data of each bone block, implant and peripheral operating rod, reduction frame and operating bed in the patient's pelvis, the high-precision magnetic navigation and positioning technology and optical tracking technology are used to collect the location information data of the patient's pelvis in real-time (focusing on the collection of coordinate points set of the patient's bone surface, the operating rod, the reduction frame and the operating bed), therefore, the patient pelvic fracture data acquisition unit is actually a high-precision optical inertial tracking system. This invention uses magnetic navigation and positioning technology, to collect real-time patients pelvic location information data, the magnetic navigation and positioning technology is to use magnetic properties to make spatial orientation judgment of objects, or the use of magnetic field and other external factors to realize patients pelvic navigation and control, it has the same principle as the magnetometers, so the essence is equivalent to the inertial sensor, further, it can also combine with optical tracking technology of optical locator to achieve optical inertial hybrid navigation and positioning. Then the mixed reality data fusion processing unit uses mixed reality technology to match patients pelvic location information data with sample fracture model, based on sample fracture model and collected patients pelvic location information data, combined three-dimensional bone deformation technique based on iteration closest points (ICP algorithm) and then reconstruct individual intelligence pelvic fracture model of patients, and using the magnetic navigation and positioning technology and the optical tracking technology to obtain pelvic fracture conditions, which allows medical staff to require tiny wounds into several implants or operating rods without patient surgery, it can accurately determine the fracture of the patient, and avoid the problems of large incision, large loss of blood and great reduction fixation difficulty in the previous pelvic reduction surgery, and to protect patients from pain, the difficulty of surgery was greatly reduced, and recovery rate and quality of life of patients are also improved and enhanced.

Preferably, the mixed reality data fusion processing unit matches the coordinate system and the relative position relationship between the implant, operating rod, reduction frame and operating bed when matching the patient pelvic location information data with the sample fracture model using mixed reality technology, and matching process is carried out by automated non-rigid image registration technology, that is, immediate position of each bone block, implant, operating rod and thereof relative position relationship are calculated in real-time during the matching process, then precise matching, to solve corresponding problems of the two-dimensional images and three-dimensional images, and using the mirror mapping results of one position image of the patient's pelvis as reduction reference parameter of the patient pelvis displacement, combined with the image mapping results of other posture images, reduction space coordinate parameters are obtained through surface registration.

Preferably, the patient pelvic fracture data acquisition unit receives the pelvic location information of the patient after the reduction operation of the patient's pelvic fracture by medical personnel or intelligent robot, the mixed reality data fusion processing unit also uses automated diagnostic techniques to diagnose overfitting after received patient pelvic fracture reduction operation. Because the data amount of the sample pelvic fracture model created according to the sample pelvis is still limited, it is easy to cause the overfitting problem in the mixed reality processing. However, the automatic diagnosis technology can effectively solve the overfitting problem and improve the accuracy of mixed reality data fusion.

Preferably, the mixed reality data fusion processing unit loads the constructed intelligent fracture model for the patient pelvic fracture state for muscle attachment condition, that is, the muscle stop point and direction of action for muscle attachment conditions (understanding of human tissue, such as skin, muscle, etc.) loaded on individualized intelligent fracture models are automatically searched based on the graph or statistical morphological model, and based on the human body tissue bounding box tree method realize automatic avoidance of the important human anatomical structures (such as blood vessels, nerves, etc.) during the operating rod implantation process, so as to avoid injury patients when the operating rod is implanted in patients.

Preferably, when the patient pelvic fracture data acquisition unit receives the patient pelvic location information after the reduction operation of the patient pelvic fracture by the intelligent robot, the mixed reality data fusion processing unit further performs intelligent reduction clinical path planning in real-time according to results of deep learning of the sample fracture model and the intelligent fracture model, so as to automatically find the optimization of clinical surgery path (note that surgery path must be to unlock of pelvic bone block first, push and pull of the reentry shift operation after unlocking), the operation path is shortest to avoid secondary injury caused by large range of movement, and at the same time, important human body anatomical structures or tissues such as blood vessels, nerves and bone blocks are effectively avoided to avoid unnecessary injuries, save operation time and improve surgical treatment effect. Even when the intelligent robot is used to replace the medical staff in the operation, it can be combined with the navigation servo control technology in the magnetic navigation and positioning technology, the real-time bone block characteristics (human tissue characteristics) can be used as servo feedback to establish servo control task, so the intelligent robot can operate according to the intelligent reduction clinical path under control of the navigation servo, and track and adjust the path in-real time until the successful pelvic reduction, which greatly improves the real-time, stability, accuracy, reliability and safety of the pelvic reduction operation.

Preferably, the intelligent robot adopts the intelligent mechanical arm based on the muscle force loading method to simulate the operation strength of the medical staff, at this time, the patient pelvic fracture data acquisition unit receives the patient pelvic location information after the reduction operation of the patient pelvic fracture by intelligent mechanical arms loaded with muscle force. After simulating the operation strength of the medical personnel with the intelligent mechanical arm, the surgical operation according to the intelligent reduction path realizes the whole intelligent automatic operation of the whole operation process, the medical personnel can not enter the operating room or only occasionally observe the medical images displayed in the reduction situation monitoring unit in the operating room, to avoid the ray irradiation of the medical personnel and ensure the safety of the medical personnel.

Figure 3:
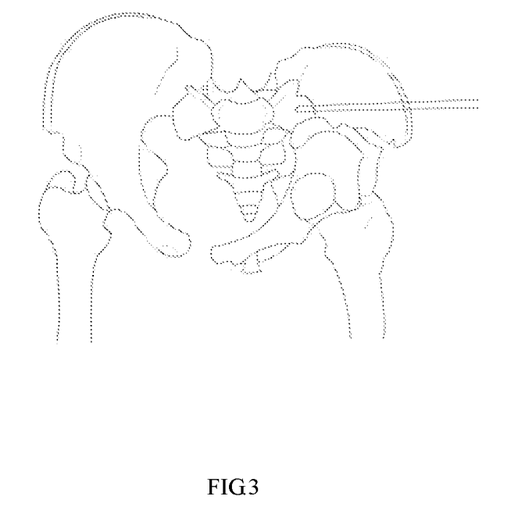
FIG. 3-FIG. 5 are medical images of three positions of the pelvis inlet position, the pelvis outlet position and the iliac oblique position displayed by the reduction situation monitoring unit of the invention.
Figure 4:
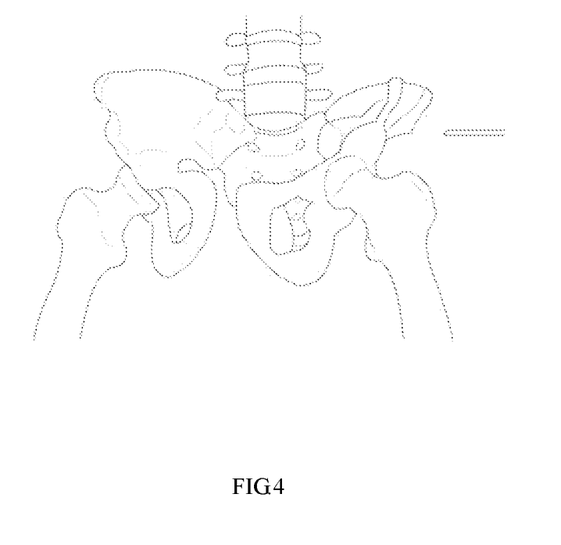
Figure 5:
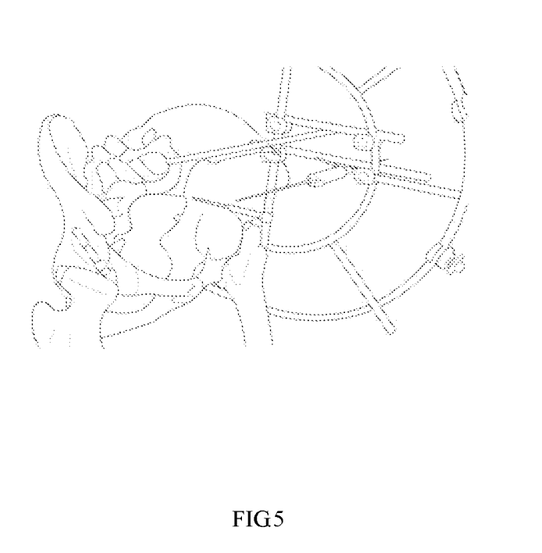

Preferably, the reduction situation monitoring unit monitors the position of the patient's pelvis in real-time, including any three or more positions combinations of pelvic front position, pelvic entrance position, pelvic exit position, obturator oblique position, iliac oblique position, LC-2 full-length image, teardrop image, obturator exit position, iliac entrance position, the sacroiliac joint image entrance position, the sacroiliac joint image exit position, the iliac wing image, the lateral pelvic image ICD line position, and the posterior column position of the pelvis lateral image, through three or more positions of the real-time observations, can effectively judge the restoration of patient pelvic fractures, if the observation of only one or two positions are successful and the reduction of the third position has not been realized, the actual reduction of stereoscopic pelvis is unsuccessful, if the observations of three or more positions are successful, the actual reduction of the stereoscopic pelvis is successful, such as FIG. 3 to FIG. 5, show the medical images of three positions of the pelvis inlet position, the pelvis outlet position and the iliac oblique position displayed by the intelligent fracture model on the reduction situation monitoring unit, as the pelvis reduction operation proceeds, the medical images of the three positions changes dynamically, when the medical images of the pelvis inlet position, the pelvis outlet position and the iliac oblique position all showed successful pelvic restoration, the actual reduction of the patient's pelvis is successful, the scheme fully solves problem of three-dimensional operation space control caused by the lack of information of real-time two-dimensional medical images, and realizes the accurate guidance of stereoscopic reduction, finally, the patient can also be given a medical fluoroscopy to test whether the results of the intelligent reduction is really successful, thus double guarantee the success of the pelvic reduction surgery. Medical staff can directly observe the reduction of the patient's pelvic position monitored by the reduction situation monitoring unit in real-time to carry on the reduction of the patient's pelvic fracture; all modules work together to realize virtual reality navigation multi-position view operation navigation tracking operation, and to confirm the consistency of pelvic position accuracy.

Figure 6:
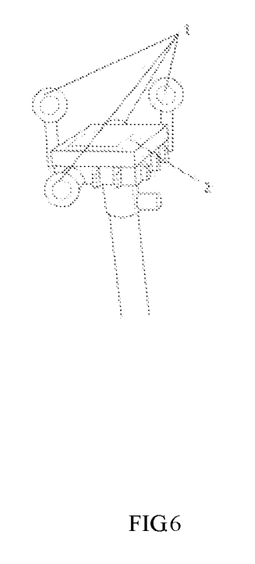
FIG. 6 is a schematic diagram of the structure of the magnetic detector and the optical locator in the present invention.
Figure 7:
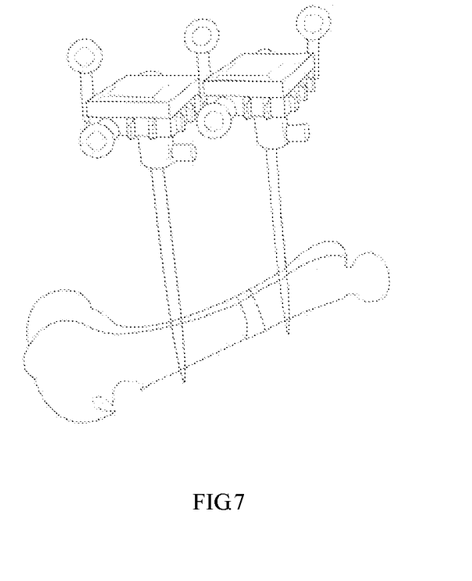
FIG. 7 is a simulation of the magnetic detector and optical locator displayed by the reduction situation monitoring unit in the present invention.

Further, the patient pelvic fracture data acquisition unit comprises a magnetic detector close to the patient's pelvic surface and an optical locator connected to the magnetic detector, as shown in FIG. 6, the magnetic detector 2 and the optical locator are linked together, the magnetic detector 2 is with embedded gyroscope and/or positioning chip, and lower end of the magnetic detector 2 is connected to the operating rod, the optical locator comprises four optical locator rods successively uniformly arranged on four sides of the magnetic detector and two optical locator rods are arranged vertically, and the other two are arranged horizontal, an optical locator ball 1 is set at the top of the optical locator rod, the optical locator ball 1 preferably employs a metal ball of diameter 1 mm and/or a pig cortical bone ball, the metal ball and/or the porcine cortical bone ball have photosensitive effect and act as the basis point for optical tracking. Further, the simulated use status of the magnetic detector and the optical locator after the intelligent fracture model is projected to the reduction situation monitoring unit is as shown in FIG. 7, thus, the connection state and relative position relationship between magnetic detector and optical locator and bone block can be fully observed, which can provide guidance for medical staff in surgical operation.

It should be noted that the above-described embodiments may make those skilled in the art more fully understand the invention, but do not limit the invention in any way. Therefore, although the present specification has been described in detail with reference to the accompanying drawings and embodiments, it should be understood by those skilled in the art that the invention can still be modified or equivalently replaced. In short, all technical solutions and improvements that do not deviate from the spirit and scope of the present invention shall all be covered by the protection scope of the present invention.

The invention claimed is:

1. An intelligent monitoring system for pelvic fracture reduction, the system comprising:
   a sample fracture model database; and
   at least one processor, wherein:
   the sample fracture model database is connected with the at least one processor,
   the sample fracture model database is configured to store a plurality of sample fracture models that are established by data of human body pelvic fracture simulated by a sample pelvis based on an automatic segmentation algorithm,
   the at least one processor is configured to collect patient pelvic location information data in real-time using magnetic navigation and positioning technology, by receiving the patient pelvic location information data from a magnetic detector and an optical locator linked with the magnetic detector, the optical locator comprising four optical locator rods arranged at four sides of the magnetic detector and four optical locator balls each located at an end of a different one of the four optical locator rods, the at least one processor is configured to automatically invoke one of the sample fracture models in the sample fracture model database corresponding to a patient pelvic fracture condition according to the patient pelvic location information data, and match the patient pelvic location information data with the invoked one of the sample fracture models using mixed reality technology to form a constructed fracture model for a pelvic fracture state of the patient, and the at least one processor is configured to load and display multiple images of the constructed fracture model in different positions in real-time for monitoring a reduction situation of different positions of the patient's pelvis in real-time through the multiple images.

2. The intelligent monitoring system for pelvic fracture reduction according to claim 1, wherein:

the at least one processor is configured to collect data from the sample pelvis to simulate human body pelvic fracture, and the at least one processor is configured to use artificial intelligence technology for automatic analysis and processing, establish a number of the sample fracture models by analyzing fracture simulation data based on the automatic segmentation, and store all the sample fracture models in the sample fracture model database.

3. The intelligent monitoring system for pelvic fracture reduction according to claim 2, wherein the at least one processor is configured to collect fracture simulation data from several angles by at least one of photographs, a two-dimensional perspective, and scanning, and the sample pelvis comprises at least one of an artificial pelvis, an animal pelvis, and a cadaver pelvis.

4. The intelligent monitoring system for pelvic fracture reduction according to claim 1, wherein:

a positioning location accuracy is within a range of 5 mm or closer and a positioning angle accuracy is within a range of 5° or closer, and the patient pelvic location information data of the patient comprises location information data of each bone block, implant and peripheral operating rod, and reduction frame in the patient's pelvis.

5. The intelligent monitoring system for pelvic fracture reduction according to claim 4, wherein the at least one processor is configured to match a coordinate system and a relative position relationship between the implant, operating rod, and reduction frame when matching the patient pelvic location information data with the sample fracture model, and matching is carried out by automated non-rigid image registration technology.

6. The intelligent monitoring system for pelvic fracture reduction according to claim 4, wherein the at least one processor is configured to receive the patient pelvic location information data of the patient after a reduction operation of the patient's pelvic fracture by medical personnel or intelligent robot, and to use automated diagnostic techniques to diagnose overfitting after the reduction operation of the patient's pelvic fracture.

7. The intelligent monitoring system for pelvic fracture reduction according to claim 4, wherein the at least one processor is configured to load the constructed fracture model for the pelvic fracture state of the patient for muscle attachment condition, based on a human body tissue bounding box tree method for automatic avoidance of human anatomy during an operating rod implantation process.

8. The intelligent monitoring system for pelvic fracture reduction according to claim 6, wherein when the at least one processor is configured to receive the patient pelvic location information data after the reduction operation of the patient pelvic fracture by the intelligent robot, and perform intelligent reduction clinical path planning in real-time according to results of deep learning of the sample fracture model and the constructed fracture model.

9. The intelligent monitoring system for pelvic fracture reduction according to claim 8, wherein the at least one processor is configured to receive the patient pelvic location information data after the reduction operation of the patient pelvic fracture by intelligent mechanical arms loaded with muscle force.

10. The intelligent monitoring system for pelvic fracture reduction according to claim 1, wherein the at least one processor is configured to monitor the position of the patient's pelvis in real-time, including any three or more position combinations of pelvic front position, pelvic entrance position, pelvic exit position, obturator oblique position, iliac oblique position, LC-2 full-length image, teardrop image, obturator exit position, iliac entrance position, a sacroiliac joint image entrance position, a sacroiliac joint image exit position, a iliac wing image, a lateral pelvic image ICD line position, and a posterior column position of a pelvis lateral image.

11. The intelligent monitoring system for pelvic fracture reduction according to claim 7, wherein when the at least one processor is configured to receive the patient pelvic location information data after the reduction operation of the patient pelvic fracture by the intelligent robot, and perform intelligent reduction clinical path planning in real-time according to results of deep learning of the sample fracture model and the constructed fracture model.

12. The intelligent monitoring system for pelvic fracture reduction according to claim 11, wherein the at least one processor is configured to receive the patient pelvic location information data after the reduction operation of the patient pelvic fracture by intelligent mechanical arms loaded with muscle force.

13. The intelligent monitoring system for pelvic fracture reduction according to claim 2, wherein the at least one processor is configured to monitor the position of the patient's pelvis in real-time, including any three or more position combinations of pelvic front position, pelvic entrance position, pelvic exit position, obturator oblique position, iliac oblique position, LC-2 full-length image, teardrop image, obturator exit position, iliac entrance position, a sacroiliac joint image entrance position, a sacroiliac joint image exit position, a iliac wing image, a lateral pelvic image ICD line position, and a posterior column position of a pelvis lateral image.

* * * * *